US008716666B1

(12) United States Patent
Demers et al.

(10) Patent No.: US 8,716,666 B1
(45) Date of Patent: May 6, 2014

(54) METHOD OF DETECTING CONTAMINANT MATERIALS IN FOOD PRODUCTS

(75) Inventors: Joseph R. Demers, North Hollywood, CA (US); Ronald T. Logan, Jr., Pasadena, CA (US)

(73) Assignee: Emcore Corporation, Albuquerque, NM (US)

( * ) Notice: Subject to any disclaimer, the term of this patent is extended or adjusted under 35 U.S.C. 154(b) by 177 days.

(21) Appl. No.: 12/813,359

(22) Filed: Jun. 10, 2010

(51) Int. Cl.
*G01J 5/02* (2006.01)
(52) U.S. Cl.
USPC .................................................. 250/339.05
(58) Field of Classification Search
USPC ................ 250/338.1–338.4, 339.01–339.15, 250/341.1–341.8
See application file for complete search history.

(56) References Cited

U.S. PATENT DOCUMENTS

| | | | |
|---|---|---|---|
| 8,026,487 B2 * | 9/2011 | Koshelev et al. | 250/341.8 |
| 2004/0155665 A1 * | 8/2004 | Arnone et al. | 324/644 |
| 2005/0100866 A1 * | 5/2005 | Arnone et al. | 433/215 |
| 2006/0054824 A1 * | 3/2006 | Federici et al. | 250/339.02 |
| 2006/0235621 A1 * | 10/2006 | Cole et al. | 702/19 |
| 2007/0235658 A1 * | 10/2007 | Zimdars et al. | 250/390.07 |
| 2011/0184654 A1 * | 7/2011 | Ben-David et al. | 702/19 |

OTHER PUBLICATIONS

Ung et al., "Comparative investigation of detection and melamine in food powers,", 2009, IEEE, 34th International Conference on Infrared, Millimeter, and Terahertz Wave, pp. 1-2.*
Hor et al., "Terahertz study of trichloroanisole by time-domain spectroscopy,", 2008, Chemical Physics, vol. 353, pp. 185-188.*
Jordens et al., "Detection of foreign bodies in chocolate with pulsed terahertz spectroscopy," 2008, Optical Engineering, vol. 47, No. 3, pp. 037003-1 to 037003-5.*
Ciurapinski et al., "Modelling of thermal emissivity of covered bulk explosive materials in the THz range," 2009, SPIE Proceedings, vol. 7485, pp. 7485p-1 to 7485p-8.*
Kurtz et al., "Frequency domain terahertz spectroscopy," 2005, IEEE Infrared and Millimeter wave and 13th International conference on Terahertz Electronics, vol. 1 pp. 76-77.*
Brenner et al., "Detection of THz radiation with semiconductor diode lasers," 2007, Applied Physics Letters, vol. 91, pp. 101107-1 to 101107-3.*
Kozlov et al., "Portable THz Spectrometers," 2006, IEEE, Infrared Millimeter Waves and 14th International Conference on Terahertz Electronics, p. 463.*
Mihoubi et al., "All-semiconductor room-temperature terahertz time domain spectrometer,", 2008, Optics Letters, vol. 33, No. 18, pp. 2125-2127.*
Brown, E.R. "A photoconductive model for superior GaAs THz photomixers," Applied Physics Letters, vol. 75, No. 6, pp. 769-771. Aug. 9, 1999. American Institute of Physics, Melville, NY.
Yeh, D.J., et al., "A new design for increased THz power from Ltg GaAs photomixers," SPIE Proc. on Terahertz and Gigahertz Photonics and Electronics II, vol. 4111, p. 124-312, Jul. 2000. SPIE, Bellingham, WA.

(Continued)

*Primary Examiner* — Kiho Kim

(57) ABSTRACT

Disclosed herein is a method of detecting a contaminant material in a food sample. The method includes irradiating a food sample with a beam of electromagnetic radiation, the beam having a plurality of frequencies in the range of about 100 GHz to about 2 THz; detecting radiation transmitted and/or reflected from the food sample; and, analyzing the detected radiation to determine the presence of contaminant material. The contaminant material may be melamine, cyanuric acid, ammeline, or ammelide.

20 Claims, 3 Drawing Sheets

(56) References Cited

OTHER PUBLICATIONS

Brown, E.R., et al., "Characterization of a Planar Self-Complementary Square-Spiral Antenna in the THz Region," Microwave and Optical Technology Letters, vol. 48, No. 3, pp. 524-529. Mar. 2006. John Wiley & Sons, Hoboken, NJ.

Harsha, S., et al., "High resolution waveguide of THz-TDS of melamine." Conference on Lasers and Electro-Optics (CLEO) 2008 paper: JWA40. Optical Society of America, Washington, DC.

Mauer, L., et al., "Melamine Detection in Infant Formula Powder Using Near-and Mid-Infrared Spectroscopy." Journal of Agricultural and Food Chemistry, vol. 57, No. 10, pp. 3974-3980. 2009. American Chemical Society, Washington, DC.

Demers et al., "An Optically Integrated Coherent Frequency-Domain THz Spectrometer with Signal-to-Noise Ratio up to 80 dB," *Proceedings of the IEEE International Topical Meeting on Microwave Photonics*, Victoria, British Columbia, 2007; 4 pgs.

\* cited by examiner

METHOD OF DETECTING CONTAMINANT MATERIALS IN FOOD PRODUCTS

REFERENCE TO RELATED APPLICATIONS

This application is related to U.S. patent application Ser. No. 12/062,772, filed Apr. 4, 2008, and U.S. patent application Ser. No. 11/796,069, filed Apr. 5, 2007, now U.S. Pat. No. 7,439,511, which is a continuation-in-part of U.S. patent application Ser. No. 11/669,685, filed Jan. 31, 2007, now U.S. Pat. No. 7,535,005.

BACKGROUND OF THE INVENTION

1. Field of the Invention

The invention relates generally to methods of detecting contaminants, and more particularly to a method of detecting contaminants in a food sample using THz spectroscopy.

2. Description of the Related Art

Recent recalls involving pet food and milk products contaminated with melamine and other contaminants have created a widespread food safety scare. This type of contamination of food products can lead to disease or death in people and animals. Recently, for example, melamine had been found in infant formula, powdered milk, pet and animal food, and other protein-based food commodities. The melamine in infant formula, for example, resulted in deaths in China. The result has been increased awareness of the hazards of melamine and a heightened need to detect its presence and other food contaminants.

Compositionally, melamine (2,4,6-triamino-1,3,5-triazine) is an organic base and a trimer of cyanamide. It has several industrial uses, including fire retardation, fertilizer, and in the production of plastics, glues, and laminates. More recently, however, melamine has been used illegally to increase the apparent protein content of food products. For example, for protein analysis tests such as Kjeldahl or Dumas, which are based on nitrogen content, some have illegally added melamine to food because melamine is rich in nitrogen.

Of course, melamine consumption can be toxic in high doses. It is thought that simultaneous ingestion of melamine and one of its analogues, cyanuric acid, may interact in the urine-filled renal microtubes and may result the formation of round, yellow crystals. These crystals block and damage the renal cells that line the microtubes, causing the kidneys to malfunction.

Given the hazards associated with melamine contamination of food products, the Food and Drug Administration (FDA) has currently imposed a limit of 1 ppm of melamine in infant formula and 2.5 ppm in other foods. The European Union (EU) has set a standard of 0.5 milligrams of melamine per kilogram body mass. In light of such stringent regulation, detection of melamine at very low concentrations is critical.

The FDA lists two principle methods for detecting melamine in food products: liquid chromatography triple quadrupole tandem mass spectroscopy (LC-MS/MS); and gas chromatography/mass spectroscopy (GC-MS). See U.S. F.D.A., Library Information Bulletin Nos. 4421 & 4423, Volume 24, October 2008. The LC-MS/MS method detects the presence of cyanuric acid and melamine in infant formula. The GC-MS method detects the presence of melamine, ammeline, ammelide, and cyanuric acid in dry protein materials. Both methods involve many steps, including extraction, filtration, centrifugation, and dilution or evaporation, after which the treated sample is then analyzed using a liquid or gas chromatography column. The LC-MS/MS method is able to screen for contaminants at concentrations as low as 0.25 µg of melamine per gram of dry infant formula. The GC-MS method can screen for the melamine and its analogs at concentrations as low as 2.5 µg of contaminant per gram of dry protein material.

While effective in identifying melamine at low concentration levels, these methods are not necessarily ideal for high-throughput testing situations, due to the process time and requirement for numerous sample treatment steps. Also, sample preparation is time-consuming and labor-intensive, as are the cleanup procedures.

Recently, near- and mid-infrared spectroscopy techniques have been used for melamine detection, in particular in infant formula powder. See Mauer et al., J. Agric. Food Chem., 57:3974-3980 (2009). The techniques are purportedly able to reach the current FDA limit of 1 ppm, but they do not appear to be as sensitive as LC-MS/MS and GC-MS, which can achieve parts-per-billion (ppb) sensitivities. While not as sensitive, these techniques offer some advantages because they are able to detect melamine much faster than LC-MS/MS and GC-MS, and with generally fewer processing steps. Overall though, near- and mid-infrared spectroscopy are still not a complete solutions to the need for high sensitivity, high throughput, rapid melamine detection. For example, there are a number of materials that can block near infrared radiation, and thus hinder detection of contaminated products hidden underneath certain materials. Furthermore, at near- and mid-infrared wavelengths, there can be scattering variations in spectrometer response that are dependent upon the particle size and shape of the powder under analysis. To counteract this, the proposed near- and mid-infrared techniques use a scatter correction process, along with a partial least-squares model to analyze the spectroscopy data. A similarly rapid, but more sensitive, and less limited technique for food contaminant detection is still desired.

SUMMARY OF THE INVENTION

Disclosed herein is a method of detecting the presence of a contaminant material in a food product using electromagnetic radiation. The method includes irradiating a food sample with a beam of electromagnetic radiation, the beam having a plurality of frequencies in the range of 100 GHz to about 2 THz. The method further includes detecting radiation transmitted and/or reflected from the food sample. The radiation detected can be analyzed to determine whether the food sample contains a contaminant material.

The contaminant material may be melamine, cyanuric acid, ammeline, ammelide, or combinations thereof. The food sample is preferably a dairy product, and more preferably infant formula. The beam is preferably an optically-generated beam. The plurality of frequencies is preferably in the range of about 400 GHz to about 1100 GHz. The contaminant under detection is preferably present in the food sample at a concentration of at least 2.5 parts per million, and more preferably at a concentration of at least 1 part per million.

In some examples, the contaminant is detected using a terahertz spectroscopy system operating at room temperature. The food sample may be tested in a packaged form, e.g., stored in one or more containers made from paper, plastics, metal, cardboard, ceramics, fabric, or combinations thereof.

The method can also include detecting the radiation transmitted and/or reflected from the food sample located behind at least one packaging layer, and preferably behind a plurality of different packaging layers. The method can also include scaqnning the beam across the food sample to detect the radiation transmitted and/or reflected from different portions of the food sample. The method can further include irradiating the food sample at different depths to detect the radiation transmitted and/or reflected from the food sample.

Additional advantages and features of the present invention will become apparent to those skilled in the art from this disclosure, including the following detailed description as well as by practice of the invention. While the invention is described below with reference to example embodiments, it should be understood that the invention is not limited thereto. Those of ordinary skill in the art having access to the teachings herein will recognize additional applications modifications and embodiments in other fields, which are within the scope of the invention as disclosed and claimed herein and with respect to which the invention could be of utility.

BRIEF DESCRIPTION OF THE DRAWINGS

These and other features and advantages of this invention will be better understood and more fully appreciated by reference to the following detailed description when considered in conjunction with the accompanying drawings wherein.

Figure 1:
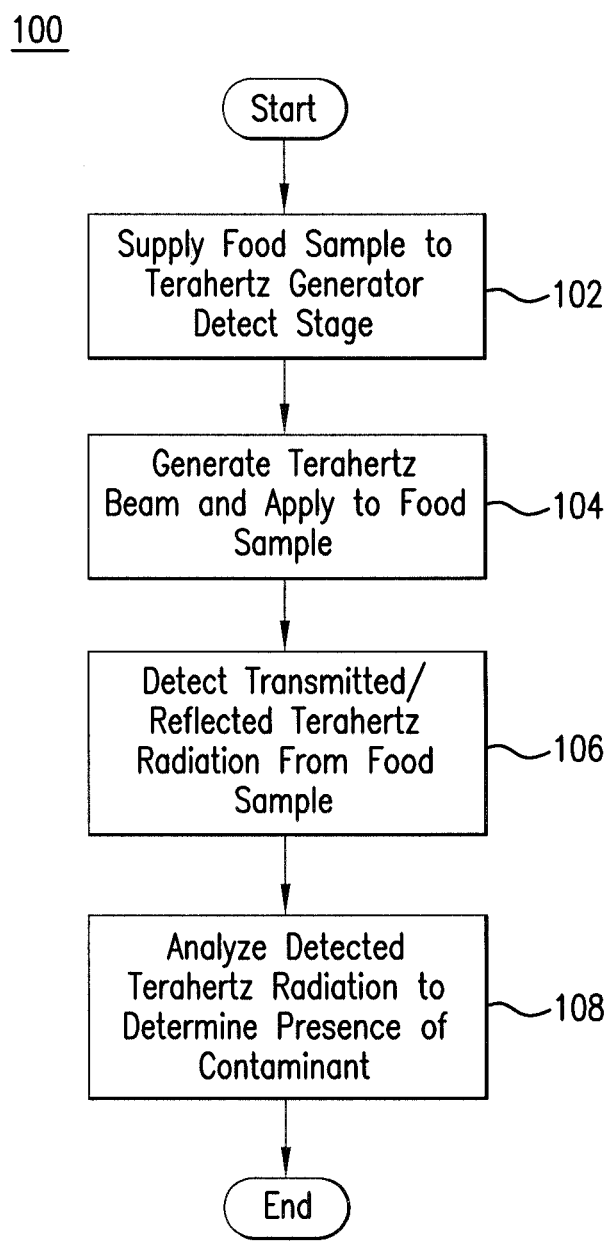
FIG. 1 illustrates a process for detecting contaminants in food samples.

The novel features and characteristics of the invention are set forth in the appended claims. The invention itself, however, as well as other features and advantages thereof, will be best understood by reference to a detailed description of a specific embodiment, when read in conjunction with the accompanying drawings.

DETAILED DESCRIPTION

Details of the present invention will now be described, including example aspects and embodiments thereof. Referring to the drawings and the following description, like reference numbers are used to identify like or functionally similar elements, and are intended to illustrate major features of exemplary embodiments in a highly simplified diagrammatic manner. Moreover, the drawings are not intended to depict every feature of actual embodiments or the relative dimensions of the depicted elements, and are not drawn to scale.

Various techniques are described for detecting a contaminant material in a food sample. These techniques generally include irradiating a food sample with an optically generated beam of Terahertz (THz) electromagnetic radiation. While the THz radiation may span the entire THz spectral range (e.g., about 100 GHz to about 3 GHz), preferably only the lower portion of that THz frequency range (i.e., about 100 GHz to about 2 THz) is used. Once the sample is illuminated, the system detects transmitted and/or reflected radiation from the food sample and produces spectral or image data, which is analyzed to determine whether a contaminant material is present in the food sample. The contaminant material can be melamine, cyanuric acid, ammeline, ammelide, or combinations thereof. The contaminant is preferably present in the food sample at a concentration of at least 2.5 parts per million, and more preferably at a concentration of at least 1 part per million.

Referring to the drawings and the following description, like reference numbers are used to identify like or functionally similar elements, and are intended to illustrate major features of an apparatus for generating a plurality of frequencies in the range of about 100 GHz to about 2 THz.

FIG. 1 illustrates an example process 100 for detecting the presence of a contaminant material in a food sample. While the example is discussed with respect to food and detecting contaminants therein, it will be appreciated that any type of detectable sample may be used. At a block 102, the food sample is provided to a THz spectroscopy system. This sample can be taken from a larger production volume and provided to the THz system via a delivery mechanism such as a vial, Petri dish, glass plate, etc. In other examples, and preferably for rapid analysis in process flow environments, the sample is examined in a deliverable form, for example, by integrating the THz spectroscopy system with the food delivery and packaging system. For example, a portable THz spectroscopy system could be retrofitted to a food conveyor or packaging system such that the THz spectroscopy system tests the food sample during regular process operations. The sample may be provided in its packaged form, where the food sample of interest is housed in a container and perhaps other housing. The sample can be provided through manual or automatic means, and continuously fed or periodically sampled, for example in a batch-wise manner. In a continuous mode, samples can pass by the detector continuously, with the detector irradiating the passing samples.

Block 104 represents the generation of the THz radiation by the spectroscopy system that is used to spectrally examine the sample from block 102. The apparatus detects the radiation transmitted and/or reflected from the food sample at block 106, where a THz frequency detector collects the transmitted and/or reflected radiation and converts it to the appropriate data. The detector may be of various types, including a scanning THz detector or array traditionally used for THz imaging. Preferably, the detector is an intensity detector.

Block 108 analyzes the detected radiation to determine the absorbance, and thus, the chemical content of the sample, in particular whether the sample has any one of a number of identifiable containments. Various methods of analysis may be executed by the block 108, including comparing the detected radiation values to a known radiation profile of the contaminant, or baselining the detected radiation values against a known, non-contaminated (pure) sample of the same food product. For the former, the radiation detected can be compared to a known library of contaminants (e.g., stored in a look-up table or other data memory storage form) to determine whether a contaminant is present in the food sample. The latter may include obtaining a characteristic absorbance spectrum of the pure food sample as a baseline. Then, the baseline from the pure food sample can be subtracted out of the detected radiation from a food sample to determine whether a contaminant is present. The block 108 may determine if a threshold amount of contaminant is present in the food sample and provide a warning signal, for example, to flag workers or inspection personnel of the contamination. In some examples, the block 108 may also determine a quality, or assurance, factor that analyzes the quality of the detected radiation data and providing a separate indication of sample data accuracy, which can change depending on noise in the detection radiation signal, intensity variations across the spectral region, and other operational conditions.

Because in the preferred examples the process 100 is non-destructive, the same food sample can be tested numerous times, such that the analysis block 108 may average detected radiation data over multiple tests of the same sample or over multiple tests taken of different samples from the same production volume. Averaging the data will help reduce noise. More robust analyses techniques, including the partial least-squares (PLS) models of Mauer et al., J. Agric. Food Chem 57:3974-3980 (2009) may be modified to develop correlation models between THz spectroscopic data and contaminant concentration. Preferably, the analysis models are designed to meet the established regulation levels for melamine detection, e.g., as low as 2.5 parts per million or as low as 1 part per million as set forth by the FDA.

The THz beam generated by block 104 includes a plurality of frequencies in the range of about 100 GHz to about 2 THz, and preferably in the range of about 400 GHz to about 1100 GHz. An example THz beam generator and spectroscopy system will now be described.

Figure 2:
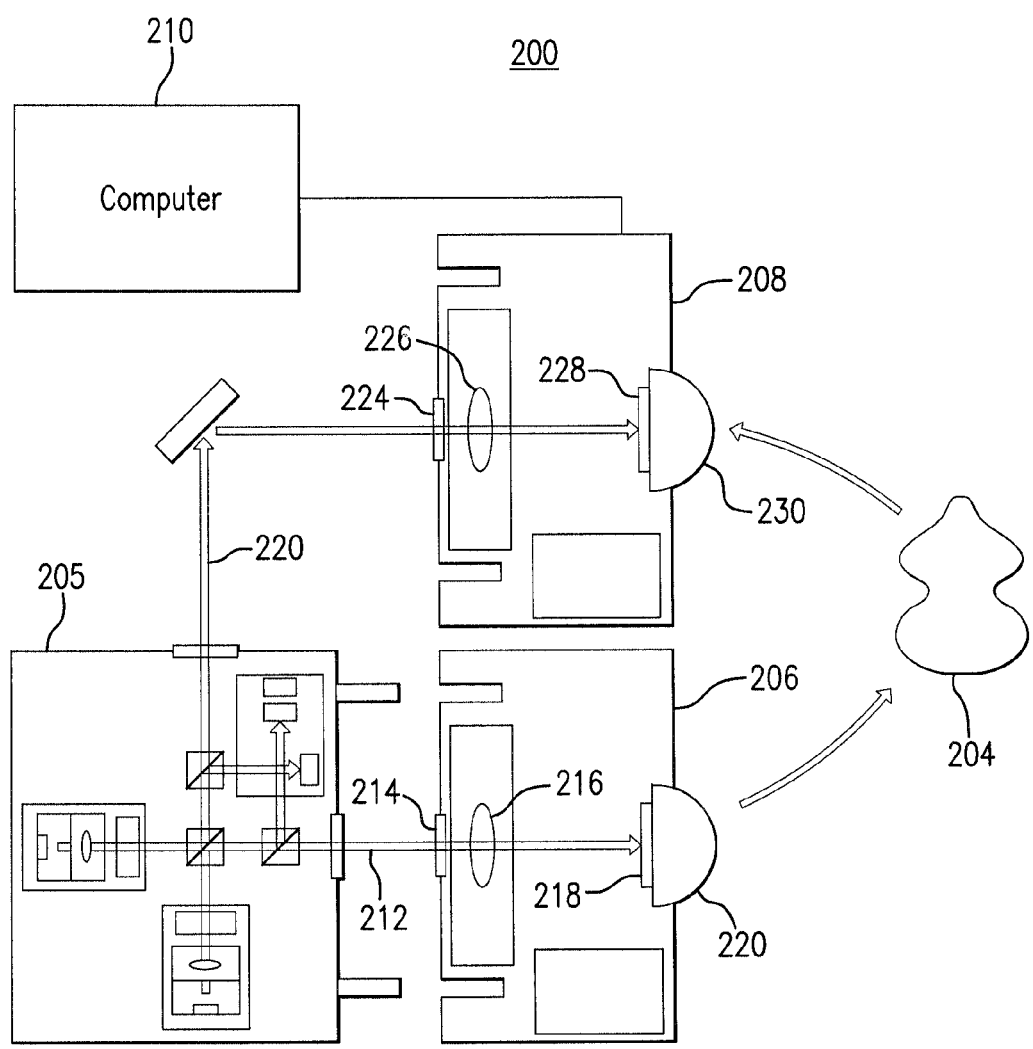
FIG. 2 is a block diagram of a THz spectrometer that may be used to implement the process of FIG. 1 and that is able to achieve desired detection levels at low terahertz frequencies; and, FIG. 3 is a graph of the absorbance spectrum for melamine and lactose powder under an example application of the THz spectrometer of FIG. 2.

FIG. 2 illustrates an example THz spectroscopy system capable of accurately characterizing contaminants in food samples, such as melamine, by using THz spectral data obtained only over the lower end of the THz spectrum. Melamine has been characterized at the higher end of the THz spectrum. See Harsha et al., "High Resolution Waveguide THz-TDS of Melamine," in *Conference on Lasers and Electro-Optics/Quantum Electronics and Laser Science Conference and Photonic Applications Systems Technologies*, OSA Technical Digest (CD) (Optical Society of America, 2008), paper JWA40. However, Harsha et al. obtained useful data only in the higher end of the THz spectrum, i.e., above 2 THz and sought to use cryogenic temperatures (77 Kelvin) to obtain sharper characterization. In fact, the data in Harsha et al. suggests that one could not detect and isolate melamine simply by focusing on the THz region below 2 THz. In contrast, the disclosed method provides for accurate characterization of contaminants in food samples at the lower end of the THz spectrum, i.e., the range of about 100 GHz to about 2 THz, and preferably in the range of about 400 GHz to about 1100 GHz.

Figure 3:
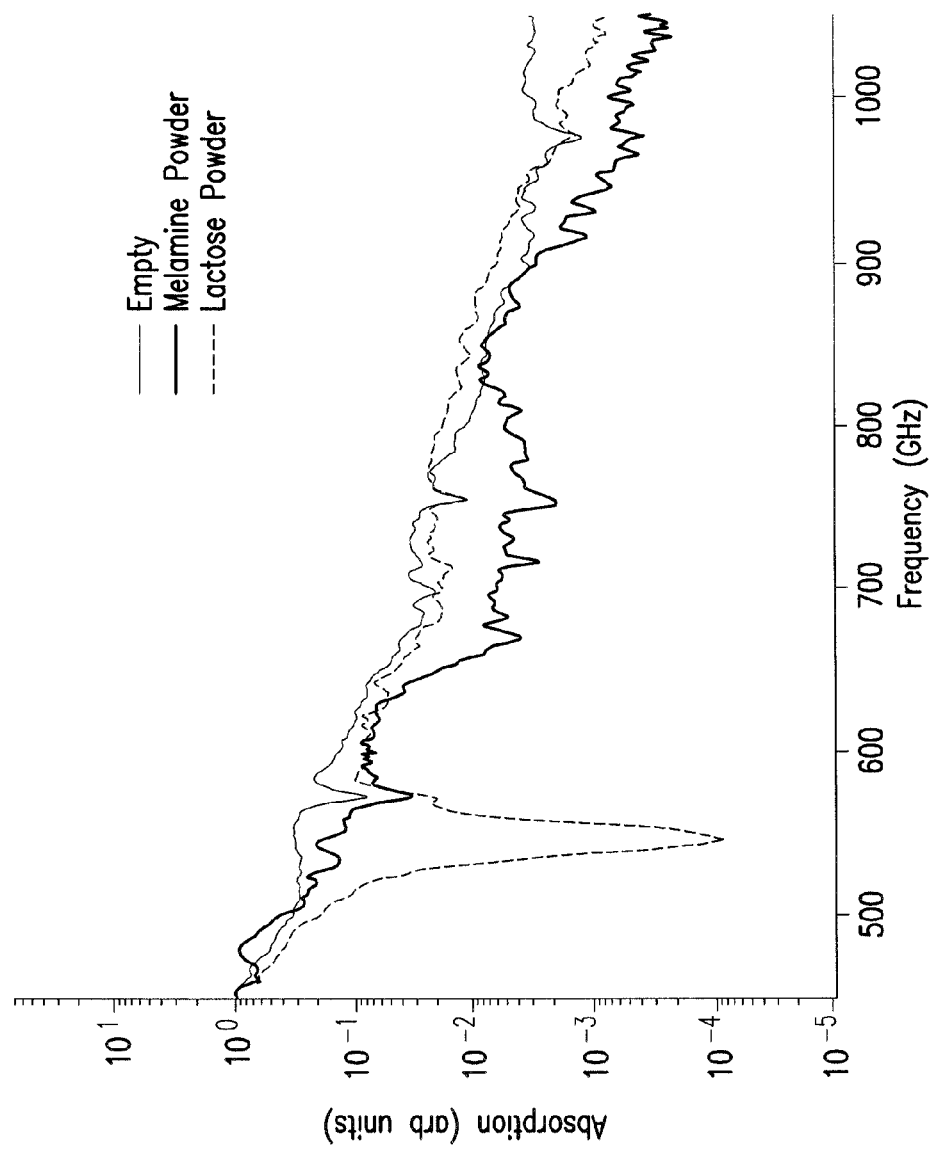

FIG. 3 is an example of an absorbance plot of lactose powder and melamine powder over about 400 GHz to 1100 GHz, as determined using the THz system of FIG. 2. FIG. 3 shows the unique absorbance data associated with melamine that can be gathered using THz spectroscopy at the lower end of the THz spectrum, if a sufficiently accurate measuring system is used. A unique absorbance spectrum can be observed for both melamine powder and the pure food sample. This unique characterization at the lower end of the THz spectrum was unexpected because Harsha et al. observed minimal characterization at the lower end of the THz spectrum. Further, characterization of the lactose and melamine powder was performed without the use of cryogenic temperatures.

The method is preferably performed at room temperature. Room temperature preferably includes temperatures in a range of about 7° C. to about 32° C., more preferably in a range of about 15° C. to about 30° C., and most preferably in a range of about 22° C. to about 26° C. Having a THz spectroscopy system able to detect melamine and other contaminants at room temperature provides greater latitude in where a detection system may be installed, as well as greater latitude in integrating the system into a high throughput operation. Room temperature operation may also reduce the cost of detection by removing the need for costly cooling (cryogenic) equipment, although in some examples cooled operation may still be desired. Room temperature operation also improves safety and can prevent damage to the food sample that may occur during processing in cryogenic temperatures.

An advantage of some implementations is that the food sample may be tested in its original-intended packaging. THz spectroscopy is particularly amenable to such testing because THz radiation is able to penetrate many types of materials that might otherwise be blocked by other spectroscopy methods. These packaging materials may include, for example, paper, plastics, metal, cardboard, fabric, and ceramics. Furthermore, the present THz spectroscopy techniques may be used to identify contaminants under numerous layers of such packaging. This would allow testing at shipyards and the like where, for example, products such as milk powder have already been packaged into individualized containers that are delivered in bulk packaging pallets housed in metal shipping containers.

Furthermore, in some examples, the THz spectroscopy system is able to scan across the food sample to detect for the presence of contaminants. This scanning allows the system to collect data across a XY-scanned plane, for example. The THz spectroscopy system may also provide a Z-axis, depth control, to allow for scanning of the food sample along different depths. In a time-resolved system, scanned THz spectroscopy may be used to map the location of contaminants along a 3D volume of the food sample. This may be particularly useful for examining food samples that are delivered in large volume quantities. This functionality also allows a single THz spectroscopy system to detect for contaminants in different containers contained within a bulk packaging container, e.g., a shipping pallet.

Returning to FIG. 2, illustrated is an example THz spectroscopy system 200 like that disclosed in application Ser. No. 12/062,772, the entire disclosure of which is hereby incorporated by reference. The system 200 preferably generates a beam having a plurality of frequencies in the range of about 100 GHz to about 2 THz, and more preferably, in a range of about 400 GHz to about 1100 GHz. The system 200 includes a THz generator 202 that illuminates a sample 204. THz energy from the generator 202 may be created using any number of THz generation techniques, for example, using short-pulsed lasers, heterodyne lasers, electronic diode multipliers, free-electron lasers, and BWOs.

Preferably the THz spectroscopy system 200 uses a frequency-domain technique, in which continuous wave (CW) THz radiation is produced through photomixing of the combined output of two single-frequency diode lasers in an ErGa: GaAs photoconductive switch (PCS) detectors configuration. The wavelength of one (or both) of the lasers is tuned to vary the THz output frequency. Preferably, the system 200 provides a coherent (homodyne) detection scheme that is able to operate at room temperature by mixing the same optical radiation from the diode lasers in a detector PCS onto which the THz signal is also incident. This provides greater sensitivity and faster data acquisition then the incoherent techniques, and preserves phase information.

This coherent frequency-domain technique has some advantages compared to the time-domain techniques, such as those of Harsha et al. These include (1) no moving parts (i.e. no mechanical scanning delay line), (2) higher frequency resolution, and (3) the ability to selectively scan specific frequency regions of interest with adjustable resolution. Also, unlike pulsed systems, CW photomixing results in all of the THz power being concentrated at a single THz frequency, thus improving spectral density and signal-to-noise ratio at that frequency.

While the overall spectrometer 200 is depicted in the block diagram of FIG. 2, a more detailed illustration of a dual laser module 205 is illustrated and discussed in incorporated U.S. application Ser. No. 12/062,772, and will not be detailed herein. Generally, two 783 nm distributed feedback (DFB) or distributed Bragg reflector (DBR) lasers with single-longitudinal-mode and single spatial-mode operation over the desired range of wavelengths are used to form two laser beams. Alternatively, one or more external-cavity tunable semiconductor lasers such as are available from Emcore Corporation could be used. The outputs from each laser are co-collimated to a very high degree of precision, using very precise frequency control of the lasers, and monitoring the laser output through digital signal processing to achieve more accurate control over the laser output beam frequencies and achieve a resolution of less than 250 MHz in a THz spectrometer.

The center wavelengths of the lasers are nominally 783 nm at 25° C., but the wavelengths may be temperature-tuned with a tuning coefficient of approximately 0.1 nm per degree Celsius. The laser outputs are used to create two co-collimating beams, a composite primary and secondary beams, at right angles to each other.

FIG. 2 is a simplified block diagram that illustrates the integration of the dual laser module 205 into a spectrometer system 200. In general, the spectrometer system 200 may employ reflection or transmission through the sample 204 by appropriate placement of a THz source head 206 and a THz detector head 208. Furthermore, the system 200 includes a computer 210, e.g., having a processor and other electronics, for determining the identity or composition of the target, and/or printing or displaying the results so that the information is readily available to the user.

In the illustrated dual laser module configuration, a primary laser beam 212 is coupled to a window 214 in the appropriately positioned source head 206, and then coupled to a lens 216 that focuses the beam 212 to a spot of approximately ten microns in diameter on the surface of a PCS 218. The optical frequency signal directed to the surface of the PCS semiconductor device produces THz radiation from the PCS 218 in the frequency range 100 GHz to over 2 THz, corresponding to the offset frequency between the lasers in dual laser module 205. The THz radiation emitted from the PCS device 218 is collimated and collected by a silicon lens 220 mounted to the source head 206. The lens 220 is preferably a hemispherically shaped structure approximately one centimeter in diameter. Additional lenses (not shown), composed of Teflon may be placed downstream of the lens 220 to collimate the RF beams into the output THz beam. Beam-shaping mirrors may also be used in lieu of or in addition to the silicon lens. The sample 204 will absorb and transmit some radiation, and in the illustrated example also reflect a portion of the radiation back in the direction of the source or user.

A secondary beam 220 from dual laser module 205 is directed to the detector head 208. The secondary beam 220, for example, is coupled to a window 224, and then coupled to a lens 226 that focuses the beam to a spot of approximately ten microns in diameter on the surface of a PCS 228. A silicon lens 230 collects transmitted or reflected radiation from the sample 204, which is then detected by PCS 228, and processed by the computer 210.

Thus, FIG. 2 illustrates an example THz spectroscopy system that may be used for contamination detection as discussed in example process of FIG. 1. Generally speaking, this system is implemented using two ErAs:GaAs PCSs in a highly compact configuration, utilizing all solid-state components and no moving parts. The system utilizes a single package integration of two 783 nm DFB laser diodes with a high-resolution wavelength discriminator. Digital signal processing electronics can provide precise frequency control and yield approximately 200 MHz accuracy of the THz signal frequency. Continuous frequency sweeping has been demonstrated with better than 500 MHz resolution from 100 GHz to 1.85 THz, thus making better resolution spectral data for contaminant analysis. The coherent detection sensitivity is shown to be in good agreement with previous theoretical predictions and yields a signal-to-noise ratio of 90 dB/Hz at 100 GHz and 60 dB/Hz at 1 THz through a path length in air of one foot. The spectrometer frequency resolution and dynamic range are suitable for applications involving analysis of chemical, biological, and explosive materials in solid-phase and gas-phase at atmospheric pressure.

The construction employs highly compact photonic integration techniques, electronic differential chopping, and room-temperature coherent THz detection. The highly integrated photonic assembly employing semiconductor diode lasers employs no moving parts and is inherently rugged and well-suited to field-deployable applications. Also, the coherent (homodyne) detection technique provides excellent SNR in agreement with theory, with much faster data acquisition times and no cryogenic cooling as required by the liquid He bolometers in more common (incoherent) THz photomixing spectrometers.

While a frequency-domain THz spectroscopy system is described, other THz spectroscopy systems may be used instead for contamination detection. These include time domain THz spectroscopy systems, for example those using a mode locked laser, (e.g., Ti:Sapphire laser or solid state laser) capable of producing a sequence of femtosecond pulses that are focused onto suitable semiconductor material to produce THz radiation. The THz signals produced by the optical pulses typically peak in the 0.5-2 THz range and have average power levels in the microwatt range and peak energies around a femtojoule. In some examples, the mode locked pulsed laser beam may be split and synchronized through a scanning optical delay line and made to strike a THz generator material (emitter) and a detector in known phase coherence. By scanning a delay line and simultaneously gating or sampling the THz signals incident on the detector, a time-dependent waveform proportional to the THz field amplitude is produced. Once generated, the THz radiation is directed to the sample 204 to be analyzed, and the detector or detector array is used to collect the signal propagated through or reflected from the object. Such measurements are made in the time domain by collecting the timed sequence of pulses and then processed by a Fourier transformation to recover the frequency domain spectral information.

In either type of system, the THz spectroscopy system can examine a particular location on the sample 204 or be designed as a scanning system that scans every point or "pixel" on the sample 205, either on a focal plane or in successive focal planes at different ranges. This may be particularly useful for detecting melamine contamination in when the sample is packaged product containing the food sample, because the THz radiation from the system 200 could be focused to or scanned over particular locations within a container for targeted analysis. In any event, the THz spectroscopy system is capable of differentiating between different materials, chemical compositions, or molecules in the interior of an object. And such detection may be performed on the surface or interior cross-sections or layers of a sample, packaged or otherwise.

In summary, the present application provides a method of detecting a contaminant material in a food sample using electromagnetic radiation over a plurality of frequencies of about 100 GHz to about 2 THz. This method enables detection of very low concentrations of contaminant material in a food sample. Further, THz radiation is able to penetrate through many materials, and may be used to irradiate a sample many feet away. The method is also preferably non-destructive enabling the sample to be tested repeatedly. THz spectroscopy is also non-ionizing.

Various modifications and improvements of the present invention may also be apparent to those of ordinary skill in the art. Thus, the particular combination of parts described and illustrated herein is intended to represent only certain embodiments of the present invention, and is not intended to serve as limitations of alternate devices within the spirit and scope of the invention.

Various aspects of the techniques and signal processing apparatus of the present invention may be implemented in digital circuitry, or in computer hardware, firmware, software, or in combinations of them. Circuits of the invention may be implemented in computer products tangibly embodied in a machine-readable storage device for execution by a programmable processor, or on software located at a network node or web site which may be downloaded to the apparatus automatically or on demand. The foregoing techniques may be performed by, for example, a single central processor, a multiprocessor, one or more digital signal processors, gate arrays of logic gates, or hardwired logic circuits for executing a sequence of signals or program of instructions to perform functions of the invention by operating on input data and generating output. The methods may advantageously be implemented in one or more computer programs that are executable on a programmable system including at least one programmable processor coupled to receive data and instructions from, and to transmit data and instructions to, a data storage system, at least one in/out device, and at least one output device. Each computer program may be implemented in a high-level procedural or object-oriented programming language, or in assembly or machine language if desired; and in any case, the language may be compiled or interpreted language. Suitable processors include, by way of example, both general and special purpose microprocessors. Generally, a processor will receive instructions and data from read-only memory and/or random access memory. Storage devices suitable for tangibly embodying computer program instructions and data include all forms of non-volatile memory, including by way of example, semiconductor devices, such as EPROM, EEPROM, and flash memory devices; magnetic disks such as internal hard disks and removable disks; magneto-optical disks; and CD-ROM disks. Any of the foregoing may be supplemented by or incorporated in, specially designed application-specific integrated circuits (ASICS).

It will be understood that each of the elements described above, or two or more together, also may find a useful application in other types of constructions differing from the types described above.

The foregoing description is given for clearness of understanding only, and no unnecessary limitations should be understood therefrom, as modifications within the scope of the invention may be apparent to those having ordinary skill in the art.

The invention claimed is:

1. A method of detecting a contaminant material in a food sample using a frequency-domain technique, comprising:
providing a portable terahertz (THz) spectroscopy system having all solid-state components and no moving parts;
operating the portable THz spectroscopy system at a temperature in a range of about 7° C. to about 32° C. to irradiate a food sample with a beam of electromagnetic radiation, the beam having a plurality of frequencies in the range of about 400 GHz to about 1100 GHz;
operating the portable THz spectroscopy system to detect radiation transmitted and/or reflected from the food sample; and
analyzing the detected radiation to determine the presence of contaminant material selected from the group consisting of melamine, cyanuric acid, ammeline, ammelide, or combinations thereof.

2. The method of claim 1, wherein the food sample is a milk product.

3. The method of claim 2, wherein the milk product is infant formula, powdered milk, or combinations thereof.

4. The method of claim 1, wherein the contaminant is present in the food sample at a concentration of at least 2.5 parts per million.

5. The method of claim 1, wherein the contaminant is present in the food sample at a concentration of at least 1 part per million.

6. The method of claim 1, further comprising performing the method at a temperature in a range of about 15° C. to about 30° C.

7. The method of claim 1, further comprising performing the method at a temperature in a range of about 22° C. to about 26° C.

8. The method of claim 1, wherein the food sample is irradiated in a packaged form.

9. The method of claim 8, wherein the packaged form comprises packaging selected from the group consisting of paper, plastic, metal, cardboard, ceramics, fabric, and combinations thereof.

10. The method of claim 1, further comprising detecting the radiation transmitted and/or reflected from the food sample located behind at least one packaging layer.

11. The method of claim 10, further comprising detecting the radiation transmitted and/or reflected from the food sample located behind a plurality of different packaging layers.

12. The method of claim 10, further comprising scanning the beam across the food sample to detect the radiation transmitted and/or reflected from different portions of the food sample.

13. The method of claim 1, further comprising irradiating the sample at different depths to detect the radiation transmitted and/or reflected from the food sample.

14. The method of claim 1, wherein the beam is an optically-generated beam.

15. A method of detecting a contaminant material in a product, comprising:
providing a portable terahertz (THz) spectroscopy system having all solid-state components and no moving parts;
operating the portable THz spectroscopy system at a temperature in a range of about 7° C. to about 32° C. to irradiate a sample of the product with a beam of electromagnetic radiation, the beam having a plurality of frequencies in the range of about 400 GHz to about 1100 GHz;
operating the portable THz spectroscopy system using a frequency-domain technique to detect radiation transmitted and/or reflected from the sample of the product; and
analyzing the detected radiation to determine the presence of the contaminant material in the sample of the product.

16. The method of claim 15 wherein analyzing the detected radiation to determine the presence of the contaminant material in the product comprises comparing the detected radiation values to a known THz radiation absorption profile of the contaminant material.

17. The method of claim 16 wherein comparing the detected radiation values to a known radiation profile of the contaminant material comprises comparing the values of the radiation detected in the THz absorption spectrum of the sample of the product to a known library of the THz absorption spectra of contaminant materials stored in a look-up table or other data memory storage form to determine whether a specific contaminant material is present in the sample of the product.

18. The method of claim 15 wherein analyzing the detected radiation to determine the presence of the contaminant material in the sample of the product comprises baselining the values of the radiation detected in the THz absorption spectrogram of the sample of the product against a known THz radiation absorption spectrogrm of a non-contaminated or pure sample of the same product.

19. The method of claim 18 wherein baselining the values of the radiation detected in the THz absorption spectrogram of the sample of the product against a known THz radiation absorption spectrogram of a non-contaminated or pure sample of the same product comprises:
- obtaining a characteristic THz radiation absorption spectrogram of the pure sample as a baseline for the pure sample; and
- subtracting out the baseline for the pure sample from the THz absorption spectrogram of the sample of the product to determine whether the contaminant material is present in the sample of the product.

20. The method of claim 15 wherein analyzing the detected radiation to determine the presence of the contaminant material in the product comprises:
- determining if a threshold amount of the contaminant material is present in the sample of the product; and
- providing a warning signal when it is determined that a threshold amount of the contaminant material is present in the sample of the product.

* * * * *